(12) United States Patent
Daly et al.

(10) Patent No.: US 10,088,896 B2
(45) Date of Patent: Oct. 2, 2018

(54) QUEASINESS MANAGEMENT FOR VIRTUAL REALITY SYSTEMS

(71) Applicant: Dolby Laboratories Licensing Corporation, San Francisco, CA (US)

(72) Inventors: Scott Daly, Kalama, WA (US); Grant Haverstock Mulliken, San Francisco, CA (US)

(73) Assignee: Dolby Laboratories Licensing Corporation, San Francisco, CA (US)

( * ) Notice: Subject to any disclaimer, the term of this patent is extended or adjusted under 35 U.S.C. 154(b) by 12 days.

(21) Appl. No.: 15/431,540

(22) Filed: Feb. 13, 2017

(65) Prior Publication Data

US 2017/0285732 A1    Oct. 5, 2017

Related U.S. Application Data

(60) Provisional application No. 62/314,504, filed on Mar. 29, 2016.

(51) Int. Cl.
| | |
|---|---|
| *G06F 3/01* | (2006.01) |
| *G06T 11/60* | (2006.01) |
| *A61B 5/0205* | (2006.01) |
| *G06T 13/40* | (2011.01) |
| *G06T 15/20* | (2011.01) |

(52) U.S. Cl.
CPC ............ *G06F 3/011* (2013.01); *A61B 5/0205* (2013.01); *G06T 13/40* (2013.01); *G06T 15/20* (2013.01); *G06T 2215/16* (2013.01)

(58) Field of Classification Search
CPC ......... G06F 3/011; G06T 15/20; G06T 13/40; G06T 2215/16; A61B 5/0205
See application file for complete search history.

(56) References Cited

U.S. PATENT DOCUMENTS

| | | | | |
|---|---|---|---|---|
| 6,839,041 | B2 * | 1/2005 | Susnfara ................. | G06F 3/012 345/158 |
| 7,288,057 | B1 | 10/2007 | Puma | |
| 8,594,381 | B2 * | 11/2013 | Fedorovskaya ...... | G02B 27/017 382/107 |
| 9,001,155 | B2 * | 4/2015 | Tamaru .................. | G02B 27/01 345/633 |
| 9,101,279 | B2 | 8/2015 | Ritchey | |
| 9,288,468 | B2 * | 3/2016 | Vaught ............... | H04N 13/0484 |
| 2009/0189974 | A1 | 7/2009 | Deering | |

(Continued)

FOREIGN PATENT DOCUMENTS

WO    2015/030797    3/2016

OTHER PUBLICATIONS

Haith, A. et al "Robustness of VOR and OKR Adaptation Under Kinematics and Dynamics Transformations" IEEE 6th International Conference on Development and Learning, Jul. 11-13, 2007, pp. 37-42.

(Continued)

*Primary Examiner* — Andrew Sasinowski

(57) ABSTRACT

Input VR imagery is received. Global motions as represented in the input VR imagery relative to a viewer of a virtual reality (VR) application is extracted. A dampening factor is applied to the global motions to generate dampened global motions. VR imagery to be rendered to the viewer at a time point is generated based on the input VR imagery and the dampened global motions.

22 Claims, 10 Drawing Sheets

(56) References Cited

U.S. PATENT DOCUMENTS

| | | |
|---|---|---|
| 2012/0182206 A1 | 7/2012 | Cok |
| 2012/0306768 A1 | 12/2012 | Bailey |
| 2013/0002813 A1 | 1/2013 | Vaught |
| 2013/0293447 A1 | 11/2013 | Bickerstaff |
| 2014/0176296 A1* | 6/2014 | Morgan ............ G06F 3/011 340/4.13 |
| 2014/0223462 A1 | 8/2014 | Aimone |
| 2014/0268356 A1 | 9/2014 | Bolas |
| 2014/0362113 A1 | 12/2014 | Benson |
| 2016/0027213 A1 | 1/2016 | Burns |
| 2016/0077547 A1* | 3/2016 | Aimone ............ G06F 3/012 345/8 |

OTHER PUBLICATIONS

Koski, T.J.T. et al "A Review of Bayesian Networks and Structure Learning" Journals of the Polish Mathematical Society, vol. 40, No. 1, 2012, pp. 53-103.

Ho, Yu-Chi, et al "A Bayesian Approach to Problems in Stochastic Estimation and Control" Office of Naval Research, Jun. 9, 1964, pp. 381-388.

Crampton, G.H. "Motion and Space Sickness" 1990, CRC Press, pp. 105-121.

Kolasinski, E. et al "An Investigation into the Predictive Modeling of VE Sickness" 1999, pp. 147-151, via Engineering Village and ACM Digital Library.

Nam Y. H. et al "Automatic Detection of Nausea Using Bio-Signals During Immerging in a Virtual Reality Environment" Conference Proc. of the 23rd Annual International Conference of the IEEE Engineering in Medicine and Biology Society, vol. 2, Oct. 25, 2001, pp. 2013-2015.

Kim, Y.Y. et al "The Application of Biosignal Feedback for Reducing Cybersickness from Exposure to a Virtual Environment" vol. 17, No. 1, Feb. 1, 2008, MIT Press Journal, pp. 1-6.

* cited by examiner

QUEASINESS MANAGEMENT FOR VIRTUAL REALITY SYSTEMS

CROSS-REFERENCE TO RELATED APPLICATION

This application claims the benefit of priority from U.S. Provisional Application No. 62/314,504, filed on Mar. 29, 2016, which is incorporated by reference in its entirety.

TECHNOLOGY

The present invention relates generally to vision devices, and in particular, to queasiness management for virtual reality systems.

BACKGROUND

Virtual Reality (VR) is well-known to induce various physiological discomforts, ranging from mild headaches to the vomit reflex. It also well-known that the main cause of this is the mismatch between the visual system input and the vestibular system (sensed with the semicircular canals for rotational movements and otoliths for translational movements). For example, the visual field may say the body should be rotating, but the vestibular system says it is stationary. This conflict in expectations can lead to nausea. In more detail, the OKR (optokinetic reflex, due to visual field motion) and VOR (vestibular ocular reflex, due to head rotations), also may be in conflict. VOR and OKR share the same vestibular nuclear neurons and oculomotor neurons, and form a servo system to stabilize vision. The VOR/OKR pathways are intertwined through the corpus callosum to the vestibular nuclei, and have internuclear connections between motor nuclei and other connections with the cerebellum.

The symptoms of discomfort grow with increasing mismatch and duration, and begin with a twinge in the stomach or feelings of light-headedness. A speculation for this effect is that humans have evolved to assume that this mismatch is caused by consumed poisons interacting with the nervous system, and therefore the best reflex is to empty the stomach quickly, hopefully getting rid of poisons, at least the portions that have not already caused the mismatch. If the causes either persist or increase, the discomfort increases causing symptoms such as mild headaches. Further increases may cause nausea, vomiting or extreme long lasting headaches (which can last over 8 hours).

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Similarly, issues identified with respect to one or more approaches should not assume to have been recognized in any prior art on the basis of this section, unless otherwise indicated.

BRIEF DESCRIPTION OF DRAWINGS

The present invention is illustrated by way of example, and not by way of limitation, in the figures of the accompanying drawings and in which like reference numerals refer to similar elements and in which.

DESCRIPTION OF EXAMPLE EMBODIMENTS

Figure 1:
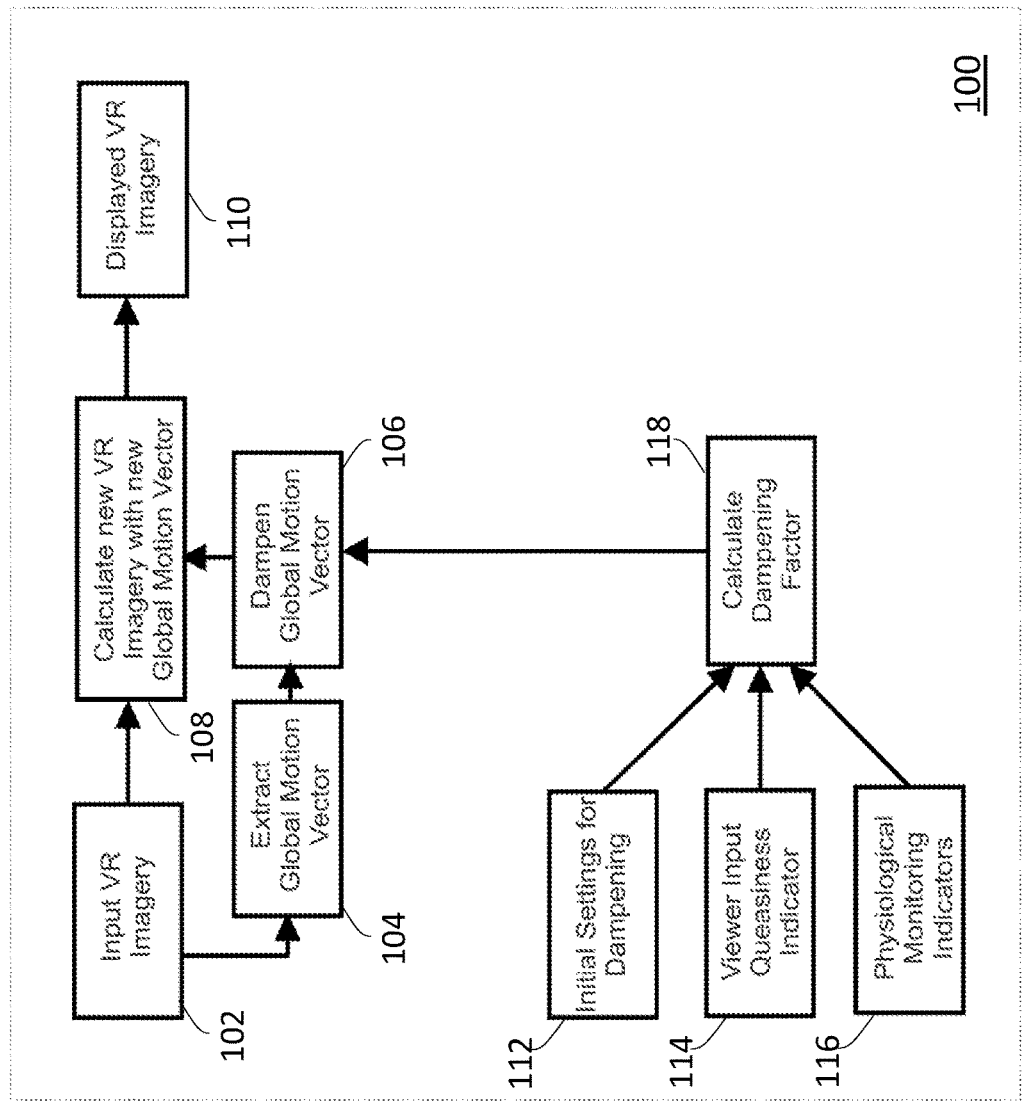
FIG. 1, FIG. 2 and FIG. 6 illustrate example queasiness management systems.

Example embodiments, which relate to queasiness management for virtual reality systems, are described herein. In the following description, for the purposes of explanation, numerous specific details are set forth in order to provide a thorough understanding of the present invention. It will be apparent, however, that the present invention may be practiced without these specific details. In other instances, well-known structures and devices are not described in exhaustive detail, in order to avoid unnecessarily occluding, obscuring, or obfuscating the present invention.

Example embodiments are described herein according to the following outline:

1. GENERAL OVERVIEW
2. GLOBAL MOTIONS IN VR IMAGERY
3. QUEASINESS MANAGEMENT IN VR
4. DAMPENING FACTOR
5. PHYSIOLOGICAL SIGNALS AND PREDICTIVE MODEL
6. QUEASINESS MANAGEMENT IN HIGHLY INTERACTIVE VR
7. EXAMPLE PROCESS FLOWS
8. IMPLEMENTATION MECHANISMS—HARDWARE OVERVIEW
9. EQUIVALENTS, EXTENSIONS, ALTERNATIVES AND MISCELLANEOUS

1. General Overview

This overview presents a basic description of some aspects of an example embodiment of the present invention. It should be noted that this overview is not an extensive or exhaustive summary of aspects of the example embodiment. Moreover, it should be noted that this overview is not intended to be understood as identifying any particularly significant aspects or elements of the example embodiment, nor as delineating any scope of the example embodiment in particular, nor the invention in general. This overview merely presents some concepts that relate to the example embodiment in a condensed and simplified format, and should be understood as merely a conceptual prelude to a more detailed description of example embodiments that follows below. Note that, although separate embodiments are discussed herein, any combination of embodiments and/or partial embodiments discussed herein may be combined to form further embodiments.

In imaging applications such as VR applications, global motions resulting from or represented in users' visual fields can be reduced to prevent nausea and headaches. Wider field of view (FOV) can increase the effects of nausea, whereas visibility of a viewer's own body portions can help reduce the effects. Depending on the level of interactivity of an imaging application, system latency may worsen the problem. For example, for the purpose of reducing/avoiding nausea/headaches, latency needs to be lowest in cases where viewer's hand interact with virtual worlds, lower when a viewer is navigating (e.g., self-navigating, navigating with constraints, etc.) through a depicted world, and may be longer if a viewer is passively viewing a virtual world. In addition, qualitative relationships between motions and nausea/headaches may be different, depending on types of motions. Accelerations are worse than translations. Rotational motions of pitch and roll are worse than yaw, at least when compared in terms of same degrees/seconds, etc.

There is also a high degree of variability on what makes people queasy. Some like extreme roller coasters or multiple-rotation axes amusement rides, while some others prefer canoeing. Some can read a book in car, while others may need Dramamine to do so. Further, those who seek higher levels in motion, rotation, thrill-related motion and even disorientation would be disappointed to have their experiences determined/dominated by those more sensitive/susceptible to the nausea symptoms.

As used herein, the term "queasiness" may refer to the earliest signs of the (e.g., undesired, abnormal, exceeding a normal range specific to a user/viewer, etc.) nausea problem, such as brief twinges or tickling in stomach, undesired light-headedness, etc.

Other approaches that do not implement techniques as described herein typically do not take individual variability in susceptibility to nauseous symptoms/effects into account. For example, the other approaches may limit levels of motions so an average viewer does not experience discomfort, limit to a field of view so that motions do not appear to be overwhelming, allow all viewers to see more of the real surrounding world (e.g., through a part of display depicting the real world, through a transparent window of an HMD to the real world, etc.) in the distance, etc. In some of the most conservative designs/approaches, motions are limited even further so the most sensitive are not affected. In order to limit the motions for the average or the most sensitive, the other approaches limit a scope of experience even for those who less or least affected by nauseous symptoms/effects, and even for those (e.g., thrill-seekers, etc.) who seek the stronger or the strongest experiences.

Unlike other approaches that do not take into account individual variability and that dampen visual experiences (e.g., VR experiences, immersive audiovisual experiences, etc.) for everyone for the comfort of the more sensitive, under queasiness management as described herein, different imageries (e.g., presenting different degrees of motions, etc.) are presented to different viewers based on the viewers' individual settings, real-time user inputs and physiological signs. For some of the more adventurous, achieving a certain amount of light-headedness or even queasiness may be desired. However, queasiness management as described herein assumes that very few viewers if any would actually desire to become nauseous or end up with a splitting headache.

As used herein, the term "queasiness management" refers to an overall approach under which imagery presented to a viewer is controlled or managed, as in color management and display management. However, instead of tailoring image rendering parameters to specific display devices as in the case of color management and display management, imagery is tailored to a specific viewer in queasiness management.

Queasiness management as described herein uses a combination of viewer-specific initial settings, real-time user inputs, physiological signs, etc., to tailor VR imagery to a viewer. The viewer's specific queasiness state at any given time (a sample/instance of a time-wise continuous queasiness state of the viewer) may be linked/related in a queasiness dynamics model to the viewer's previous queasiness state and a previous active control input (e.g., a previous dampening factor, etc.) and may be linked/related in an observation model to viewer-specific initial settings, real-time user inputs, time-varying physiological signals, etc. If the real-time user inputs, physiological signs, the viewer's previous queasiness state, a previous active control input (e.g., a previous dampening factor, etc.), etc., lead to a prediction that the viewer's next queasiness state would be above or would be on a queasiness state trajectory that would exceed the viewer's queasiness tolerance level (e.g., an upper limit of a normal range specific to the viewer, etc.), relative motions (e.g., accelerations, translations, rotations, etc.) between the viewer and upcoming imagery to be rendered to the viewer would be dampened with an adaptively determined active control input (e.g., a dampening factor, etc.). The relative motions will be increasingly dampened if necessary, for example, as indicated by the viewer's new adaptively determined next queasiness states to be above or on a queasiness state trajectory that exceed the viewer's queasiness tolerance level.

Thus, under techniques as described herein, physiological signals (e.g., physiological monitoring indicators, etc.) are explicitly analyzed in a predictive model (e.g., the dynamics model of queasiness state, the observation model, etc.), which allows a queasiness management system to estimate and predict current and upcoming levels of nausea or queasiness states and to control the future direction of a viewer's specific and dynamic queasiness state trajectory. Mitigation of occurrences of queasiness states beyond the viewer's normal range of queasiness state can be enforced by the queasiness management system based on the predicted/anticipated queasiness states. Motions in a virtual world or a remote-presence world as seen by the viewer can be dampened if necessary for the purpose of queasiness management.

Past histories of some or all of physiological signals, predicted queasiness states, active control inputs, etc., can be stored in tangible storage media. These histories can be analyzed in real time or in non-real time to determine whether queasiness management is successful or effective in a VR session or a specific part thereof, whether an amount of an active control input should be adjusted up or down for a specific viewer for similar physiological signals and/or similar previous queasiness states, etc.

A queasiness management system as described herein can be implemented with any in a variety of time resolutions to apply active control inputs to relative motions between a viewer and imagery displayed/rendered. For example, dampening motions based on the active control inputs can be timely performed as needed every few milliseconds, every tens of milliseconds, every fractions of a second, every one or more seconds, etc. The active control inputs can also be finely tuned based on a dynamically predicted trajectory of queasiness state. When the predicted trajectory of queasiness state anticipates that future queasiness states without applying a certain amount of active control would cross a threshold (e.g., an upper limit of a viewer's normal range, etc.), the queasiness management system may apply at least the certain amount of active control (e.g., as represented by a dampening factor, etc.) to prevent, or reduce the likelihood of, the viewer having undesired nauseous feeling.

As used herein, a viewer's normal range (of queasiness state) may refer to a range from no or little undesired effects or symptoms to a maximum tolerable queasiness specific to the viewer. The viewer's normal range may be binary, non-binary, normalized, numeric, percentile-based, quartile-based, statistical deviation based, etc. In some embodiments, the viewer's normal range may represent a range below a threshold (e.g., a maximum tolerable queasiness, a maximum tolerable level of nausea, an upper limit, etc.) above which the viewer is likely to feel undesired effects or symptoms. In a non-limiting example, the viewer's normal range may be represented by a galvanic skin response (GSR) range specific to the viewer. In another non-limiting example, the viewer's normal range may be multi-dimensional (e.g., a GSR range, one or more non-GSR ranges, etc.) with one of dimensional components represented by a galvanic skin response (GSR) range specific to the viewer and with others of dimensional components represented by other physiological signals. The threshold for the viewer may be determined experimentally. For example, the viewer's physiological signals (e.g., GSR, heart rate, etc.) and feedbacks/opinions (e.g., user input in real time or non-real time, etc.) were recorded and surveyed in past or test sessions. The viewer's specific threshold for the viewer's normal range may be determined based at least in part on comparing the viewer's physiological signals and feedbacks/opinions with those collected from viewers in a user population. The viewer may be (e.g., statistically, etc.) determined to be extremely susceptible, moderately susceptible, slightly susceptible, not susceptible, etc., to undesired effects or symptoms for queasiness. The viewer's threshold may be placed in a certain quartile of the user population for susceptibility, may be placed in a certain deviation from the statistical mean for susceptibility, may be placed in a normalized scale, etc.

Additionally, optionally, or alternatively, the viewer's threshold may be determined at least in part on the viewer's initial settings that may be collected in non-real time before the viewer uses a VR application as described herein.

In some example embodiments, mechanisms as described herein form a part of a media processing system, including but not limited to any of: mobile device, virtual reality system, augmented reality system, heads up display device, helmet mounted display device, CAVE-type system or wall-sized display, video game device, display device, media player, media server, media production system, camera systems, home-based systems, communication devices, video processing system, video codec system, studio system, streaming server, cloud-based content service system, a handheld device, game machine, television, cinema display, laptop computer, netbook computer, tablet computer, cellular radiotelephone, electronic book reader, point of sale terminal, desktop computer, computer workstation, computer server, computer kiosk, or various other kinds of terminals and media processing units.

Various modifications to the preferred embodiments and the generic principles and features described herein will be readily apparent to those skilled in the art. Thus, the disclosure is not intended to be limited to the embodiments shown, but is to be accorded the widest scope consistent with the principles and features described herein.

2. Global Motions in VR Imagery

FIG. 1 illustrates an example queasiness management system 100 that can operate with a variety of VR applications such as VR cinema applications, etc. In some embodiments, the system (100) comprises a number of processing entities such as a dampening factor generator 118, an imagery motion extractor 104, a motion pathway generator 106, a dynamic VR imagery generator 108, etc., each of which may be implemented collectively or individually with one or more computing processors.

As used herein, VR cinema applications may refer to a type of VR applications that are implemented as VR enhancements or extensions to panoramic image viewing applications (e.g., IMAX like viewing application, head mounted display (HMD) applications, etc.). A VR cinema application can provide not only up to an extreme field of view for better immersion, but also timely responses to head turnings or movements. In a VR cinema application, a viewer's head rotation/shaking can cause imagery to be newly revealed at a relatively large scale. Additionally, optionally, or alternatively, in such an application, a viewer's physiological tremor or head shaking can cause disocclusion (e.g., image reconstruction, image revealing, etc.) of previously occluded objects or visual details to be newly revealed at a relatively fine scale for the purpose of providing the viewer a realistic 3D viewing experience.

In some VR cinema applications, a viewer can change the viewer's spatial relationships (e.g., viewport, viewing angles, etc.) relative to objects depicted in the VR scene; further, the viewer may be able to change the time direction or timeline of a depicted story or the viewer's time-wise navigation through the VR scene. In some other VR cinema applications, while a viewer can change the viewer's spatial relationships (e.g., viewport, viewing angles, etc.) relative to objects depicted in the VR scene, the viewer may not change the time direction or timeline of a depicted story or the viewer's time-wise navigation through the VR scene. In these other VR cinema applications, a time sequence of positions of a camera that captures the VR scenes is preset (e.g., moving in a certain spatial trajectory of a rail or a rollercoaster on which the camera is mounted, etc.). Interactivity is reduced to some extent in VR cinema applications. This type of relatively low interactivity VR applications may be referred to as "linear", in reference to linear video editing.

In some VR cinema applications, the maximum field of view (FOV) supported by imagery presented to a viewer (e.g., through a display such as an HMD, etc.) is represented by a specific angle such as 180 angular degrees (e.g., hemispheric, etc.). In some other VR cinema applications, the maximum field of view (FOV) supported by imagery presented to a viewer is represented by a 360 angular degrees (e.g., fully spherical, etc.), which may be used to allow complete omnidirectional viewing. Additionally, optionally, or alternatively, either the floor or the zenith or both can be omitted in some VR cinema applications.

In some embodiments, queasiness management can be implemented by manipulating input VR imagery to limit (e.g., global, etc.) motions of what is displayed in VR cinema applications. As used herein, global motions may refer to (e.g., uniform, congruent, etc.) motions of all objects (or image features) present in a viewer's entire field of view, as opposed to local (or intra-image) motions of objects or persons depicted in the VR imagery.

By way of example but not limitation, input VR imagery may depict a soccer game in which a viewer may represent a spectator. Local motions in this example may refer to motions of soccer players relative to one another as depicted in the input VR imagery. Global motions, on the other hand, may refer to motions of all the players and including the playing field (or image details) in the viewer's field of view. Thus, global motions are motions of the viewer relative to the input VR imagery as represented in the viewer's field of view. Alternatively, global motions are motions of the input VR imagery as represented in the viewer's field of view relative to the viewer.

In some VR cinema applications, the viewer's translational motions may represent or duplicate a time sequence of preset or constrained translational motions of the camera that captures the input VR imagery. While navigating through VR scenes depicted in the VR imagery with the preset translational motions of the camera that captures the VR imagery, the viewer's angular motions may be dynamically occurring in the VR cinema applications as the viewer can change viewing angles from time to time, for example, by rotating a display (e.g., an HMD, a wearable computing device, etc.) which provides the viewer a time sequence of possibly different viewpoints to the input VR imagery.

In some VR cinema applications, neither the viewer's translational motions nor the viewer's angular motions are required to represent or duplicate a time sequence of preset or constrained translational or angular motions of the camera that captures the input VR imagery. For example, the viewer can navigate through VR scenes depicted in the VR imagery with bobbing motions, which may or may not represent or duplicate preset translational motions of the camera that captures the VR imagery.

The input VR imagery in the VR cinema applications is to be rendered for specific parameters (e.g., viewpoint, position, field of view, head orientation, left view, right view, aspect ratios, sizes, etc.) of the display used by the viewer to view the input VR imagery. A motion pathway of the viewer can influence and at least in part determine the specific parameters (e.g., viewpoint, position, field of view, head orientation, left view, right view, etc.) of the display used to render the input VR imagery. As used herein, a motion pathway of a viewer refers to a time sequence of specific relative motions of the viewer relative to input VR imagery as represented in the viewer's field of view, or alternatively a time sequence of specific relative motions of the input VR imagery as represented in the viewer's field of view relative to the viewer. The motion pathway may be a time sequence of some or all of: the viewer's linear positions, the viewer's angular positions, the viewer's translational velocities, the viewer's rotational velocities, the viewer's translational accelerations, the viewer's rotational accelerations, etc.

In some embodiments, the system (100) adaptively manipulates (or sets) a specific motion pathway of the viewer in relation to input VR imagery using a dynamics model and an observation model to estimate/predict/infer the viewer's queasiness state based on the viewer's previous queasiness state, a previous active control input, viewer-specific initial settings, real-time user inputs, physiological signs, etc.

Motions such as global motions, relative motions in a motion pathway, etc., may be represented by motion vectors. For example, linear and/or angular positions in a motion pathway can be represented by respective motion vectors in the form of linear and/or angular displacement vectors, which may be defined in relation to a reference linear position (e.g., an origin of a coordinate system, etc.) and/or a reference angular position (e.g., x axis of the coordinate system, etc.). Translational and/or rotational velocities in a motion pathway can be represented by respective motion vectors in the form of translational and/or rotational velocity vectors, which may be defined or derived as respective rates of changes in linear and/or angular displacement vectors. Translational and/or rotational accelerations in a motion pathway can be represented by respective motion vectors in the form of translational and/or rotational acceleration vectors, which may be defined or derived as respective rates of changes in translational and/or rotational velocities. In some embodiments, rotations, or rotational motion vectors, can be decomposed into multiple linear translational motion vectors. It should be noted that components of a motion pathway as described herein may be described in any of a variety of representations, among which a (e.g., real valued) vector representation represents only one non-limiting example. In some embodiments, representations of some or all components of a motion pathway as described herein may use a quaternion representation that uses a combination of scalar and (e.g., imaginary) vector parts.

In some embodiments, some or all of the positions, velocities and accelerations in a viewer's motion pathway may be adaptively controlled/determined based on an active control input (e.g., a dampening factor) adaptively and iteratively determined using dynamics model and observation models that link the viewer's queasiness state to the viewer's previous queasiness state, a previous active control input, viewer-specific initial settings, real-time user inputs, physiological signs, etc.

In some embodiments, some or all of velocities and accelerations in a viewer's motion pathway may be controlled/determined based on an active control input (e.g., a dampening factor) adaptively and iteratively determined using dynamics model and observation models that link the viewer's queasiness state to the viewer's previous queasiness state, a previous active control input, viewer-specific initial settings, real-time user inputs, physiological signs, etc.

By way of example but not limitation, input VR imagery depicts a VR scene in which a viewer may be represented as a person/camera sitting in a bobbing boat. The bobbing of the boat would cause an overall irregular oscillation (e.g., with an amplitude of a sine wave, etc.) in global motions between the viewer and the VR scene in the viewer's (e.g., entire) field of view. For some (e.g., those without "sea-legs") the bobbing motion would lead to motion sickness, while for others it makes the scene feel more realistic.

The input VR imagery may be either optically captured, computer generated, or mixed (composited) with both optically captured and computer generated imagery. A director may determine an original motion pathway in the VR world or scene for the purpose of producing the input VR imagery for release. However, the original motion pathway as determined by the director may have overly aggressive motion for specific viewers.

In some embodiments, the system (100) determines the viewer's director-specified global motions in the original motion pathway, as if the viewer would be placed on the original motion pathway. Global motions in a motion pathway (e.g., a director-specified motion pathway, a dynamically generated adaptive motion pathway, etc.) are not local motions of individual objects relative to one another within the VR world, but rather (overall) motions between the viewer and the VR world represented in the viewer's field of view. In some embodiments, the system (100) can determine global motions (e.g., director-specified global motions, global motions originally depicted in input VR imagery, etc.) using an optical flow algorithm.

In some embodiments, the system (100) uses the dynamics model to predict a specific viewer's queasiness state at any time point in a sequence of time points based on viewer-specific initial settings, real-time user inputs, physiological signs, etc., and to generate/calculate a dampening factor for each time point in the sequence of time points in relation to the specific viewer's queasiness state estimated/predicted for that time point.

For a thrill seeker whose threshold for a corresponding normal range of queasiness state is relatively high as compared with other viewers, the system (100) likely estimates/ predicts the thrill seeker's queasiness states as within the thrill seeker's normal range. Thus, for the thrill seeker, the system (100) may apply no or little dampening (e.g., with a unity dampening factor value) to the global motions as specified in the input VR imagery. In some embodiments, the system (100) may even apply a dampening factor value that increases global motions at some time points for the thrill seeker that appears to be unchallenged as indicated/ predicted by the thrill seeker' queasiness states for these time points.

For a specific viewer whose threshold for a corresponding normal range of queasiness state is relatively low as compared with other viewers, the system (100) likely estimates/ predicts the specific viewer's queasiness states at some time points as out of the specific viewer's normal range. Thus, for the specific viewer, the system (100) may apply dampening (e.g., with a fractional dampening factor value) to the global motions as specified in the input VR imagery at some time points to generate less global motions in imagery of the specific viewer's field of view if the specific viewer appears to be on a state trajectory that the specific viewer's queasiness states would exceed the specific viewer's normal range for these time points.

In some embodiments, the dampening factor generator (118) comprises software, hardware, a combination of software and hardware, etc., configured to receive initial settings 112 for dampening. In some embodiments, the initial settings (112) are relatively coarse settings, for example, determined from questioning a viewer to assess where the viewer is on an overall scale of queasiness susceptibility or motion sensitivity. The questioning of the viewer may be done in any of numerous manners from most explicitly to perhaps surreptitiously (possibly with web interest correlation, etc.). A possible question to assess the viewer may be "can you read a book in a moving car?" If the viewer answers no, then the viewer may be assigned a high susceptibility that results in strong dampening for the viewer. Another possible question to assess the viewer may be "do you do skydiving?" If the viewer answers yes, then the viewer may be assigned a low susceptibility that results in no or little dampening for the viewer. Additionally, optionally, or alternatively, the initial settings may also include motion thresholds (e.g., maximum angular degrees per second in a rotational motion, maximum g value in an acceleration motion, etc.) specified for the viewer.

While VR imagery (e.g., with global motions possibly dampened, etc.) is presented to a viewer, the dampening factor generator (118) receives real time or near real time physiological monitoring indicators 116 of the viewer. The real time or near real time physiological monitoring indicators (116) of the viewer can be represented as one or more time sequences of physiological monitoring indicator values over a VR session, over a specific time interval, while the system (100) is operating in certain operational modes (e.g., default, as selected by the viewer, etc.). In some embodiments, the real time or near real time physiological monitoring indicators (116) of the viewer are time sampled or polled relatively frequently, for example, every half a second (or at a frequency of 2 Hz), every one fifth second (or at a frequency of 5 Hz), etc. Different types of physiological monitoring indicators as described herein may or may not be sampled/generated at the same rate in time.

In some embodiments, acquisition of the physiological monitoring indicators (116) by the system (100) with sensors operating in conjunction with the system (100) requires no action from the viewer, and is the most preferred in the longer term. For example, the viewer's HMD can be designed to perform some or all of a variety of physiological monitoring operations that are used to generate some or all of the physiological monitoring indicators (116), due to the HMD's proximity to the head, scalp, eyes, and face. Also, in some system configurations of the system (100), it may be practical to interface with other physiological sensing devices that may be on a glove or other haptic devices.

Additionally, optionally, or alternatively, while the VR imagery is presented to the viewer, the dampening factor generator (118) receives viewer input 114 entered by the viewer as a subjective queasiness indicator from the viewer. In some embodiments, the viewer input (114) can be a continuous input like a dial, slider, etc. In some embodiments, the viewer input (114) can be a time-of-use input, such as tapping a button if any feeling of undesired queasiness is felt.

In some embodiments, the viewer input (114) may comprise asynchronous events (e.g., sparsely) generated by the viewer, for example, through a user interface device such as a knob, a button, etc., operated by the viewer. Additionally, optionally, or alternatively, the viewer input (114) may comprise asynchronous events generated by user interface devices/components that are non-contact based, such as infrared or ultrasonic imagers that can perform gesture control. These asynchronous events may comprise event data (generated based on the viewer input) that indicates whether the viewer is subjectively feeling a relatively high degree of queasiness, whether the viewer is subjectively feeling unchallenged by the VR imagery, whether the viewer is subjectively feeling that the VR imagery is over aggressiveness, etc.

In some embodiments, the dampening factor generator (118) implements a queasiness dynamics model that links a viewer's queasiness state at the next time point in a sequence of time points to some or all of the initial settings (112), the viewer input (114), the physiological monitoring indicators (116), etc., received at time points before the next time point. Using the queasiness dynamics model, the dampening factor generator (118) can integrate the initial settings (112), the viewer input (114), the physiological monitoring indicators (116), etc., into an overall dampening factor to dampen the global motion vectors. More specifically, using the queasiness dynamics model, based on the initial settings (112), the viewer input (114), the physiological monitoring indicators (116), etc., received at the time points before the next time point, the dampening factor generator (118) can predict/ estimate the viewer's queasiness state at the next time point in the sequence of time points. Based on the predicted/ estimated queasiness state, the dampening factor generator (118) can generate a corresponding dampening factor to be used by the motion pathway generator (106) to decide whether global motions of the VR imagery should be dampened and what an extent of global motion dampening is if any.

In some embodiments, a dampening factor as described herein represents an overall factor, for example a scalar normalized from 0 to 1. The dampening factor can apply to one or more motion vectors such as one or more of: translational and/or rotational velocity vectors, translational and/or rotational acceleration vectors, etc. In some embodiments, different motion vectors can be assigned with different weight factors. In some embodiments, different components (e.g., yaw, pitch, roll, forward motion along a spatial trajectory, backward motion along a spatial trajectory, motion along an x direction, motion along a y direction, motion along a z direction, etc.) of a motion vector can be assigned with different weight factors. The dampening factor can be applied to the motion vectors, or components therein, in combination of respective weight factors assigned to the motion vectors, or the component therein.

In some embodiments, a dampening factor represents a vector that comprises components to be applied to different motion vectors. In some embodiments, a dampening factor may represent a construct other than a scalar or a vector. In an example, the dampening factor may be in a matrix representation and may be applied to different motion vectors through matrix-based operations. In another example, the dampening factor may be represented as a functional and may be applied to different motion vectors in functional relationships.

In some embodiments, the imagery motion extractor (104) of FIG. 1 comprises software, hardware, a combination of software and hardware, etc., configured to receive input VR imagery 102, for example, from one or more of video decoders, video sources, media files, cloud-based content providers, media bitstreams, video signals, etc. In some embodiments, the imagery motion extractor (104) extracts/determines global motions as represented in the input VR imagery (102), as specified by a director, etc., for example, through an optical flow algorithm. Additionally, optionally, or alternatively, the imagery motion extractor (104) may determine the global motions using image metadata received with the input VR imagery (102). In an example, the image metadata may specify or describe a motion pathway of a camera that was used to acquire the input VR imagery. In another example, the image metadata may specify or describe a director specified motion pathway implemented in the input VR imagery.

In some embodiments, the motion pathway generator (106) comprises software, hardware, a combination of software and hardware, etc., configured to receive the dampening factor as a time sequence of dampening factor values adaptively determined by the dampening factor generator (118); to receive the global motions in the input VR imagery (102) as determined by the imagery motion extractor (104); etc. In some embodiments, the motion pathway generator (106) applies the dampening factor to the global motions in the input VR imagery to generate new global motions (which may be represented by new global motion vectors). By way of generating the new global motions with the dampening factor, the motion pathway generator (106) creates or selects a specific motion pathway for the viewer.

In some embodiments, the dynamic VR imagery generator (108) comprises software, hardware, a combination of software and hardware, etc., configured to receive the same input VR imagery (102) received by the imagery motion extractor (104); receive the viewer's specific motion pathway as determined by the motion pathway generator (106); generate/calculate new VR imagery based on the input VR imagery (102) and the viewer's specific motion pathway; etc. In some embodiments, the new VR imagery may be sent to, or used by, a display (e.g., the viewer's HMD, a wearable computing device, etc.) to cause the new VR imagery to be rendered to the viewer, for example, as displayed VR imagery 110. For example, the new VR imagery generated by applying dampened motion vectors that are different from the global motions of the input VR imagery can be sent to actual display inputs within the viewer's HMD. The motion vectors to be dampened in the new VR imagery may be translational and rotational motions of VR worlds in the input VR imagery. The new VR imagery may be further mapped to the viewer's HMD (e.g., in the form of two 2D images sent to each of left and right eye views of the HMD).

The input VR imagery may be (e.g., optically captured, computer graphics, etc.) imagery made in advance for a specific HMD. In some embodiments, the new VR imagery that is rendered/displayed may be generated or adapted directly from the input VR imagery with dampened motion vectors without (e.g., real time, near real time, dynamically, etc.) incorporation of additional (e.g., optically captured, computer graphics, etc.) imagery portions/features other than those come with or represented in the input VR imagery. In some embodiments, the new VR imagery that is rendered/displayed may be generated or adapted in part from the input VR imagery with dampened motion vectors with (e.g., real time, near real time, dynamically, etc.) incorporation of additional (e.g., optically captured, computer graphics, etc.) imagery portions/features other than those come with or represented in the input VR imagery.

The input VR imagery may be (e.g., optically captured, computer graphics, etc.) three-dimensional (3D) or multiview imagery. In some embodiments, the new VR imagery that is rendered/displayed may be generated or adapted directly from the input VR imagery with dampened motion vectors without (e.g., real time, near real time, dynamically, etc.) adjustment/change of depth/disparity information carried by the input VR imagery. In some embodiments, the new VR imagery that is rendered/displayed may be generated or adapted in part from the input VR imagery with dampened motion vectors with (e.g., real time, near real time, dynamically, etc.) adjustment/change of depth/disparity information carried by the input VR imagery.

3. Queasiness Management in VR

Figure 2:
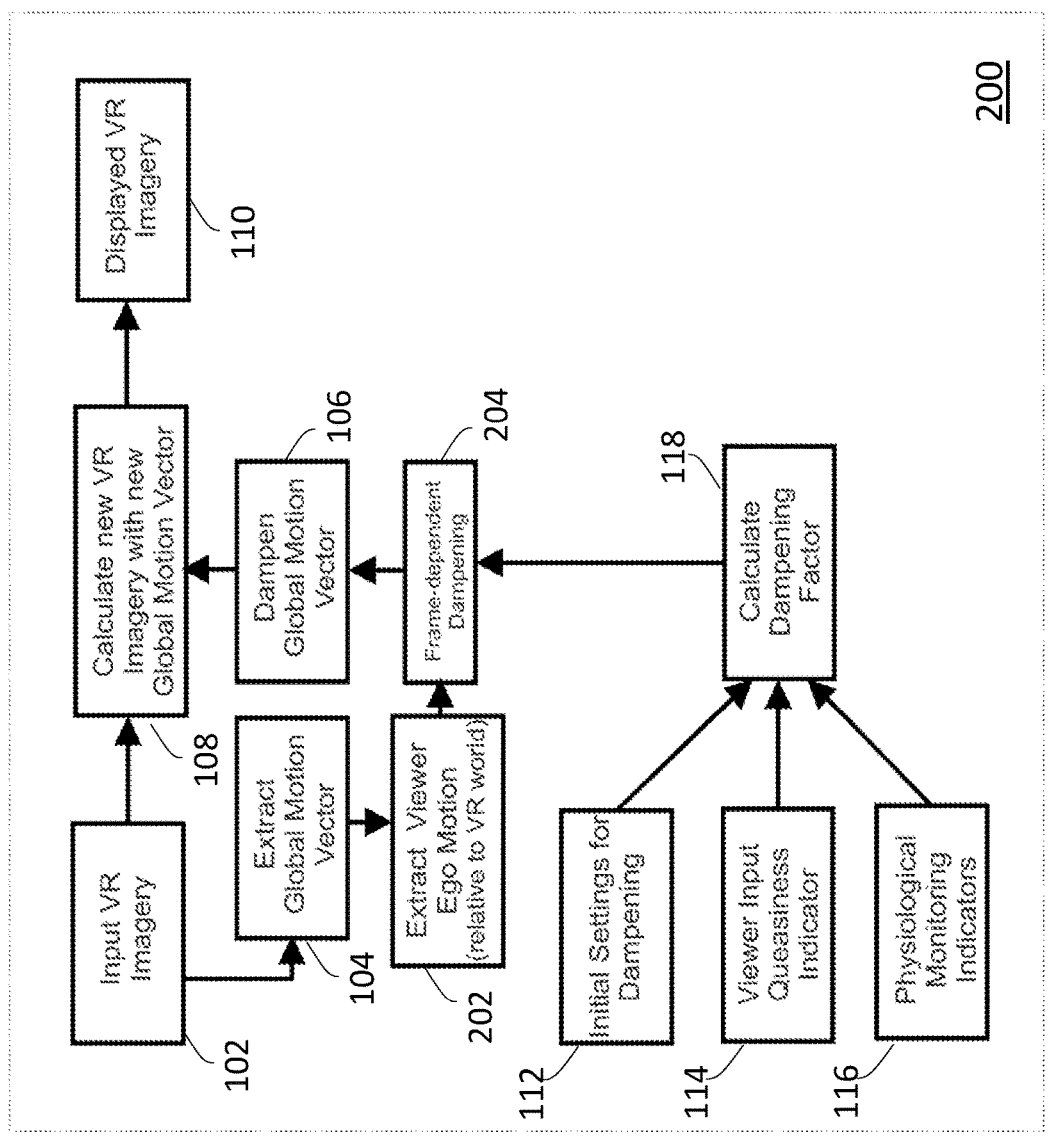

FIG. 2 illustrates an example queasiness management system 200 that can operate with a variety of VR applications. In some embodiments, the system (100) comprises a number of processing entities such as a dampening factor generator 118, an imagery motion extractor 104, a motion pathway generator 106, a dynamic VR imagery generator 108, an ego-motion extractor 202, a frame-dependent motion dampener 204, etc., each of which may be implemented collectively or individually with one or more computing processors.

In some embodiments, the system (200) may be implemented by the system (100) of FIG. 1 with additional processing entities such as the ego-motion extractor (202), the frame-dependent motion dampener (204), etc. The viewer's ego motions can be used to determine in part the view's viewpoints to the input VR imagery. Additionally, optionally, or alternatively, the viewer may carry image acquisition devices that acquire real time imagery at least a part of which may be incorporated (e.g., in real time, in near real time, dynamically, etc.) with the input VR imagery in actual VR imagery to be displayed to the viewer. The system (200) can be used in VR applications that take into account both (e.g., director-specified, etc.) global motions in input VR imagery as well as a viewer's ego motions (e.g., in real time, in near real time, sampled every half a second, sampled every few image frames, etc.).

In some embodiments, the ego-motion extractor (202) comprises software, hardware, a combination of software and hardware, etc., configured to receive the viewer's motion data, for example, from motion sensors, positional sensors, orientation sensors, etc.; based on the viewer's motion data, determine the viewer's ego motions; etc. In some embodiments, the viewer's ego motions are represented by a time sequence of motion vectors (e.g., translational motion vectors, angular motion vectors, etc.). In an example, the viewer's ego motions may be the viewer's head movements (e.g., shaking, etc.). In another example, the viewer's ego motions may be the viewer's upper body movements (e.g., upper body turning, etc.). In yet another example, the viewer's ego motion may be the viewer's walking, running, etc. In a further example, the viewer's ego motion may be the viewer's autonomous movement (e.g., head movement, etc.) on a constrained spatial trajectory such as a virtual rail, etc.

The time sequence of motion vector that represents the viewer's ego motion may, but is not required to, be sampled or polled at a time resolution comparable to a frame rate (e.g., 120 frames per second, etc.) of the input VR imagery. The time sequence of motion vectors may comprise motion vectors obtained at a relatively small frequency/tempo such as every half a second (or at a frequency of 2 Hz), every one fifth second (or at a frequency of 5 Hz), etc. Different types and/or different components of motion vectors as described herein may or may not be sampled/generated at the same rate in time.

In some embodiments, the ego-motion extractor (202) comprises software, hardware, a combination of software and hardware, etc., configured to correlate the ego-motions with the global motions extracted from the input VR imagery to generate frame-dependent motions. For example, the viewer's ego-motion at a particular time point (e.g., the next time point in a sequence of time points after the current time point, etc.) that corresponds to one or more image frames (e.g., comprising image content to be shown to the viewer at the next time point, etc.) in the input VR imagery may be correlated with the global motion extracted from the one or more image frames to generate frame-dependent motions for the one or more image frames.

As used herein, frame-dependent motions may refer to a type of global motions in which a viewer's ego-motions have been correlated with global motions extracted from image frames in input VR imagery. In some embodiments, a frame-dependent motion vector that in part or in whole represents a frame-dependent motion can be generated by vector summation of a first motion vector that represents in part or in whole an ego-motion of the viewer and a second motion vector that represents in part or in whole a global motion extracted from one or more image frames in the input VR imagery.

In some embodiments, the frame-dependent motion dampener (204) receives a dampening factor as a time sequence of dampening factor values adaptively determined by the dampening factor generator (118); applies the dampening factor to the frame-dependent motions to generate new frame-dependent motions (which may be represented by new frame-dependent motion vectors). In some cases, the frame-dependent motions may be below a threshold (which may be specific to the viewer) and thus the global motions in the input VR imagery need not be dampened; the new frame-dependent motions may be the same as the (undampened) frame-dependent motions. This may be best assessed by taking into account the viewer's ego-motions together with the global motions in the input VR imagery. In some cases, even when there may be substantial global motions in the input VR imagery, but due to the viewer's ego motions, the overall frame-dependent motions of the viewer relative to the VR world depicted in the input VR imagery may be below the threshold that indicates the viewer is likely to feel discomfort; the new frame-dependent motions may be the same as the (undampened) frame-dependent motions. In some embodiments, the system (200), or the dampening factor generator (118) therein, may implement a method/algorithm to determine/assess the dampening factor at a relatively fine time scale up to an individual determination for each image frame. However, a dampening factor as described herein is not required to be determined per image frame. In some embodiments, the dampening factor can be determined at a frequency (e.g., 2 Hz, 5 Hz, etc.) slower than a frame rate of image frames represented in the input VR imagery. In some embodiments, the dampening factor is calculated for a scene, a subdivision (e.g., a set of image frames, etc.) of a scene, one or more scenes, etc.

In some embodiments, the motion pathway generator (106) comprises software, hardware, a combination of software and hardware, etc., configured to receive the new frame-dependent motions as determined by the frame-dependent motion dampener (204). Using the new frame-dependent motions generated with the dampening factor, the motion pathway generator (106) creates or selects a specific motion pathway for the viewer. Such a specific motion pathway for the viewer may comprise new global motions to be implemented in the new VR imagery to be generated from the input VR imagery. In some embodiments, the new global motions may be computed as differences between the viewer's ego motions and the dampened frame-dependent motions. In some embodiments, a new global motion vector that represents in part or in whole a new global motion to be implemented in the new VR imagery can be generated by performing vector subtraction of a motion vector that represents in part or in whole an ego-motion of the viewer from a dampened frame-dependent motion vector that in part or in whole represents a dampened frame-dependent motion.

In some embodiments, the dynamic VR imagery generator (108) comprises software, hardware, a combination of software and hardware, etc., configured to receive the same input VR imagery (102) received by the imagery motion extractor (104); receive the viewer's specific motion pathway as determined by the motion pathway generator (106); generate/calculate the new VR imagery based on the input VR imagery (102) and the viewer's specific motion pathway; etc. In some embodiments, the new VR imagery may be sent to, or used by, a display (e.g., the viewer's HMD, a wearable computing device, etc.) to cause the new VR imagery to be rendered to the viewer, for example, as displayed VR imagery 110. For example, the new VR imagery generated by applying dampened motion vectors that are different from the global motions of the input VR imagery can be sent to actual display inputs within the viewer's HMD. The motion vectors to be dampened in the new VR imagery may be translational and rotational motions of VR worlds in the input VR imagery. The new VR imagery may be further mapped to the viewer's HMD (e.g., in the form of two 2D images sent to each of left and right eye views of the HMD).

4. Dampening Factor

In some embodiments, motions dampened under techniques as described herein may comprise three translational motions and three rotational motions. The three translational motions can be represented by translational velocities and/or translational accelerations. The three rotational motions can be represented by rotational velocities and/or rotational accelerations. Of these motions, some motions are more problematic (or more prone to cause nausea or queasiness) than others; the worst may be pitch motions especially the nose-dive or speed-drop type of pitch motions, which is worse than the lift-off type of pitch motions; the next may be roll motions; the least discomforting may be yaw motions (spinning). All of these rotational motions can lead to discomfort/queasiness symptoms, but in terms of unit angular degree and/or angular second these rotational motions have different effects (e.g., a ratio of 2 to 1, etc.). Of the translational motions, forward-backward motions (e.g., along a z-axis, along a radius axis, etc.) may be the worst; discomfort/queasiness symptoms may be induced for accelerations and decelerations more than for steady speeds.

In some embodiment, a dampening factor as described herein may be set in accordance to various strengths of these types of motions in causing discomfort/queasiness symptoms, for example as a vector instead of a scalar. Thus in these embodiments, the dampening factor used to control/modulate/dampen global motions of VR imagery may be a vector comprising dampening factor components that vary as functions of types of motions. In some embodiments, different weight factors are assigned to different types of motions. In some embodiments, these weight factors do not depend on individual viewers; the same set of weight factors may be assigned to different types of motions for all viewers. In some embodiments, these weight factors depend at least in part on individual viewers; for example, a first set of weight factors may be assigned to different types of motions for a first viewer, whereas a second different set of weight factors may be assigned to different types of motions for a second different viewer.

Figure 3:
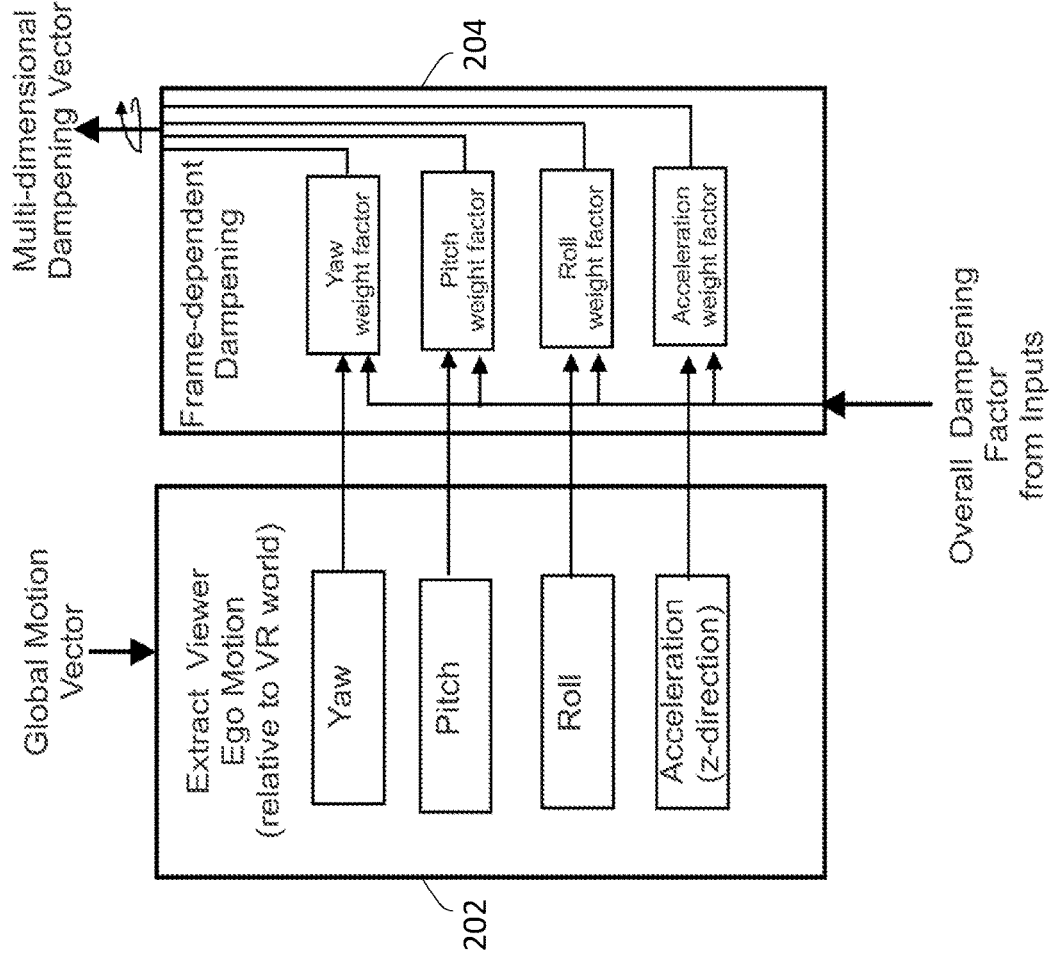
FIG. 3 illustrates an example of dampening motions using weight factors.

FIG. 3 illustrates an example of dampening different types of motions using different weight factors. In some embodiments, motions to be dampened may be rotational motions such as yaw, pitch, roll, etc., and translational motions such as acceleration in a z-direction (e.g., an up-down direction, etc.). An ego-motion extractor (e.g., 202 of FIG. 2) may be used to generate frame-dependent motions of these types that are to be dampened. In some embodiments, a frame-dependent motion dampener (e.g., 204 of FIG. 2) may receive an overall dampening factor (e.g., as a scalar, etc.) from a dampening factor generator (e.g., 118 of FIG. 1 or FIG. 2, etc.). The frame-dependent motion dampener (204) generates a new dampening factor vector whose components may be derived as respective products of the overall dampening factor and individual weight factors (for the types of motions that are to be dampened) in a set of weight factors. These individual weight factors may be assigned to the types of motions such as yaw, pitch, roll, acceleration in the z-direction, etc. The frame-dependent motion dampener (204) may apply the new dampening factor vector or a transpose thereof to frame-dependent motions to generate dampened frame-dependent motions.

5. Physiological Signals and Predictive Model

Figure 4A:
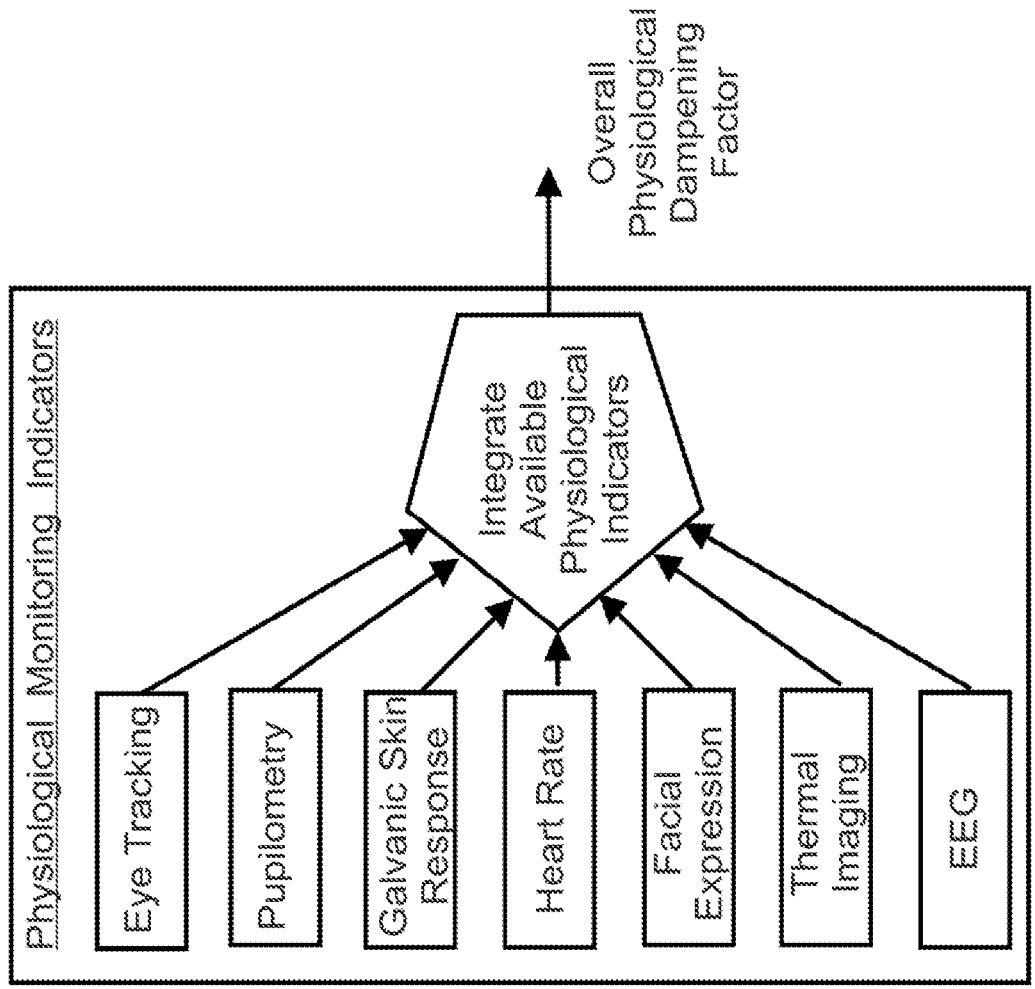
FIG. 4A illustrates example physiological monitoring indicators.

FIG. 4A illustrates example physiological monitoring indicators including but not limited to only any of: those related to eye tracking, pupilometry, galvanic skin response, heart rate, facial expression, thermal imaging, electroencephalogram (EEG), etc. In some embodiments, these and other available physiological inputs may be used as a main basis for estimating/predicting a viewer's queasiness state and for dampening motions in VR imagery if necessary. The physiological monitoring indicators may be integrated into an overall (e.g., physiological, etc.) dampening factor in any of a variety of methods. For example, the physiological monitoring indicators can be linearly combined into the overall dampening factor by a weighted summation. Additionally, optionally, or alternatively, the physiological monitoring indicators can be integrated into the overall dampening factor via machine learning and statistical models (e.g., ADABOOST, neural networks, Gaussian mixture models (GMMs), Hidden Markov models (HMMs), Support Vector Machines (SVMs), etc.).

Figure 4B:
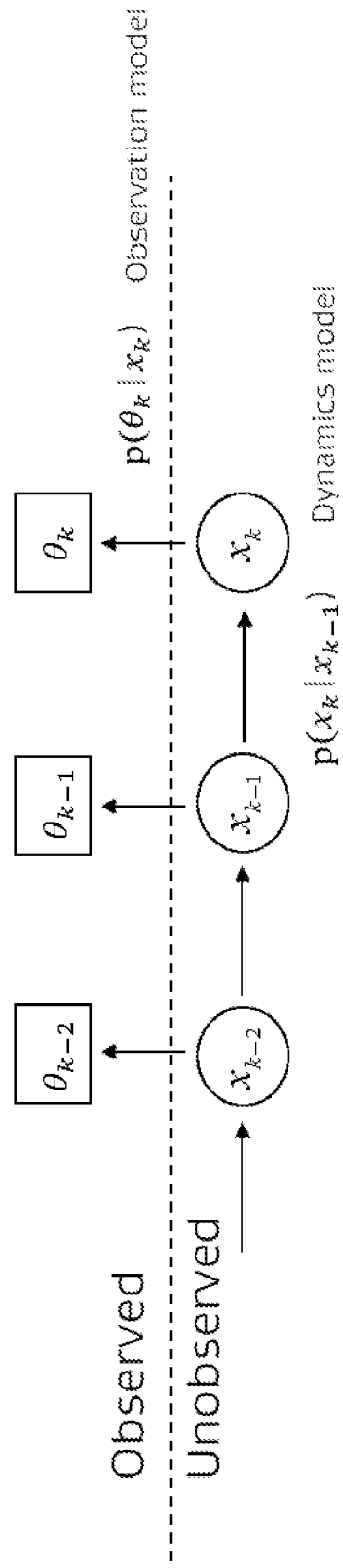
FIG. 4B and FIG. 4C illustrate example integrating physiological measurements into an overall dampening factor.
Figure 4C:
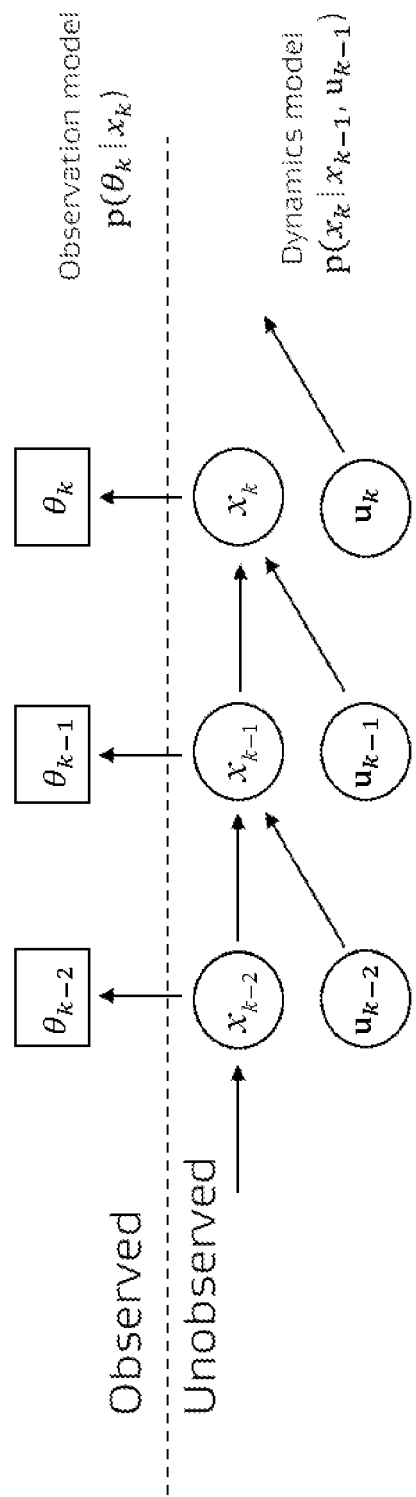

By way of example but not limitation, FIG. 4B and FIG. 4C illustrate example details of integrating physiological measurements as represented by physiological monitoring indicators into an overall dampening factor using a dynamics model that links the overall dampening factor with viewer-specific initial settings, real-time user inputs, physiological signs, etc. In some embodiments, techniques as described herein can be used to perform optimal control operations with an estimator (e.g., a Kalman filter based estimator, etc.) and a linear-quadratic-Gaussian (LQG) controller.

The level of nausea experienced by a subject, or a viewer's queasiness state, in a VR application environment can be modeled in the dynamics model as a time-varying state variable that is hidden from direct observation. The time-varying state variable is not a viewer's subjective assessment of the viewer's (e.g., past, present, etc.) queasiness state, for example, from asking the viewer or an observer directly. Rather, the time-varying state variable represents an objective queasiness state (e.g., past, present, future, etc.) predicted/estimated based on the physiological monitoring indicators. Thus, the time-varying state variable as described herein may be able to predict oncoming queasiness before the viewer self even notices anything. The "hidden" state variables can be estimated from observations (that are inherently noisy) made in the VR application environment (e.g., physiological measurements on the viewer's body, etc.).

In some embodiments, at least some of techniques as described herein can be implemented to use a state-space characterization that falls into a general framework of a recursive Bayesian estimation problem. Such a framework may comprise a dynamics model of a queasiness state, denoted as X, in combination with an observation model that relates a physiological variable, denoted as $\theta$, to X, in order to predict the upcoming (or the next) queasiness state. The predicted queasiness state may range from no undesired queasiness symptoms or effects at all to slight queasiness to headaches to vomiting.

In some embodiments, the dynamics model may be assumed to be a Markov process. Both X and $\theta$ may be multi-dimensional random variables; the dynamics model and the observation model are probabilistic. At each time sample, an estimate of the distribution of X is generated by optimally combining the initial estimate of the dynamics model with the information from the observation model. In some embodiments, the framework uses statistical and machine learning approaches for time series modeling such as directed acyclic graphs (Koski and Noble, 2012), etc. In some embodiments, when X and $\theta$ (and their additive measurement noises) are jointly Gaussian, and the dynamics model and the observation model use a linear relationship, the solution to the recursive Bayesian estimation problem becomes a Kalman filter (Ho and Lee, 1964).

In some embodiments, either or both of the dynamics model of the queasiness state and the observation model that relates the queasiness state to physiological variables/measurements can be nonlinear including but not limited to only periodic behaviors, among other possible nonlinearities. Therefore, in these embodiments, some or all of the techniques as described herein may use a relatively general recursive Bayesian implementation.

A duality (or correspondence) between optimal controllers and optimal estimators exists, as controlling/dampening an amount of motions of VR imagery displayed to a viewer effectively regulates the level of nausea as represented by the queasiness state up or down. Accordingly, the dynamics model should be augmented to capture both passive dynamics (e.g., occur without dampening, etc.) as well as effects of an active control input related to controlling/dampening the amount of motion of the VR imagery displayed to the user. More specifically, the next queasiness state, $X_{k+1}$, can be specified as a function of or dependent on both the previous queasiness state, $X_k$, and the most recent active control input, $u_k$. As used herein, the active control input of FIG. 4C may be an overall dampening factor represented by a scalar variable, an overall dampening factor represented by a vector variable, etc., such as illustrated in FIG. 4A.

As illustrated in FIG. 4C, the active control input, denoted as $u_k$, evolves in time along its state space trajectory (e.g., within a normalized range, in a linear or non-linear scale, etc.). The current value or the most recent value of the active control input can be integrated into the dynamics model and used accordingly to perturb a trajectory of the queasiness state, in order to control the queasiness state within a desired range (e.g., as specified in viewer-specific initial settings, etc.) specific to the viewer.

Figure 5:
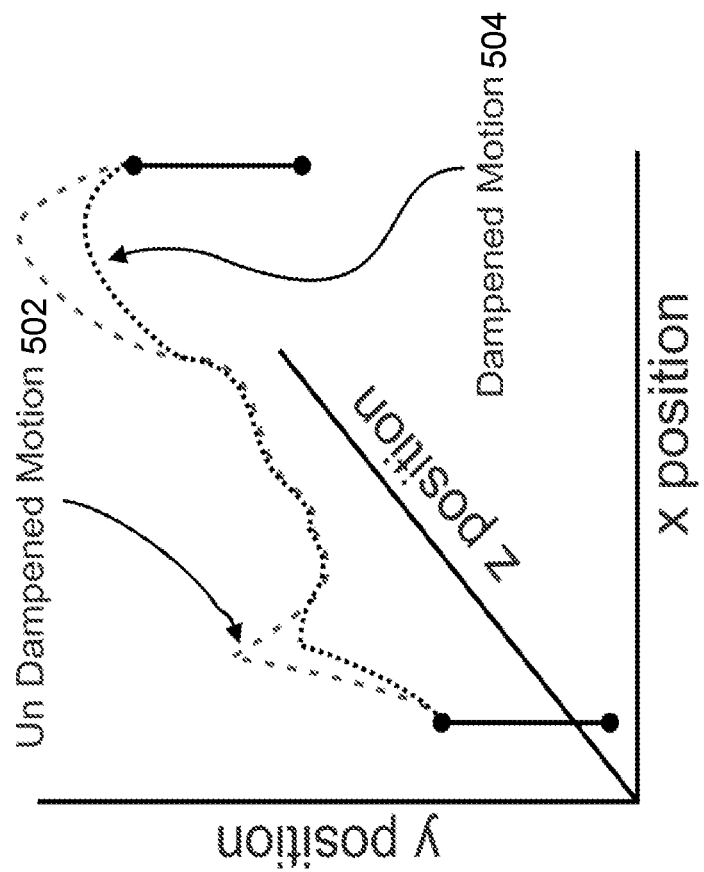
FIG. 5 illustrates an example dampening process of motions.

FIG. 5 illustrates an example dampening process of motions. By way of example but not limitation, motions involved in this dampening process may be translational, and may be represented by x, y and z Cartesian coordinate values or positions in a three-dimensional (3D) space. The dashed line represents global motions extracted from input VR imagery, whereas the dotted line represents dampened motions implemented in new VR imagery generated under techniques as described herein. The global motions may be represented as a first motion pathway 502 as represented by a first temporal pathway, a first pathway parametrized with respect to time, etc., through the 3D space. The dampened motions may be represented as a second motion pathway 504 as represented by a second temporal pathway, a second pathway parametrized with respect to time, etc., through the 3D space.

Techniques as described herein can be used to dampen translational motions as well as rotational motions. In an example, the x, y and z coordinate values of FIG. 5 may represent translational motion values (e.g., translational velocities or accelerations along spatial dimensions of a physical space depicted in VR applications, etc.). In another example, the x, y and z coordinate values of FIG. 5 may represent rotational motion values (e.g., rotational velocities or accelerations related to pitch, yaw and roll in a physical space depicted in VR applications, etc.).

In some embodiments, to prevent jittery movements and fluctuations, the second motion pathway (504) representing the dampened motions may be smoothened by a simple low-pass filtering using a FIR filter, or with an IIR filter, or with more advanced techniques like Kalman filtering. In some embodiments, filtering can be applied to translational motions as well as rotational motions in a Cartesian-separable manner, such as by using 1-D filters on each of the axes represented in the 3D space of FIG. 5 in succession (or in parallel) followed by cascading.

6. Queasiness Management in Highly Interactive VR

A variety of VR applications including but not limited to VR applications of high interactivity can be supported under techniques as described herein. Example highly interactive VR applications include game applications with VR imagery entirely generated from computer graphics as if a viewer is virtually present in a virtual world (or a game environment) depicted in the computer graphics. Some other highly interactive VR applications may be remote-presence VR applications where the viewer's movements control the cameras in the remote scene. The remote presence application primarily uses optically captured imagery, as opposed to computer graphics, as if a viewer is remotely present in a (e.g., remote) real world in which image acquisition devices (e.g., cameras, etc.) at the viewer's represented positions in the real world acquire the optically captured imagery in real time, in near real time, etc. The real world as described herein refers to a physical locale from which VR imagery is acquired (e.g., optically by cameras, etc.), even though the viewer may not be physically present at the physical locale.

In these types of VR applications of high interactivity, management or control of a viewer's queasiness state may be performed through manipulation (e.g., dampening if necessary, etc.) of the viewer's motions represented in a virtual or real world. This will then consequently limit the motions of what is displayed in the VR applications.

Figure 6:
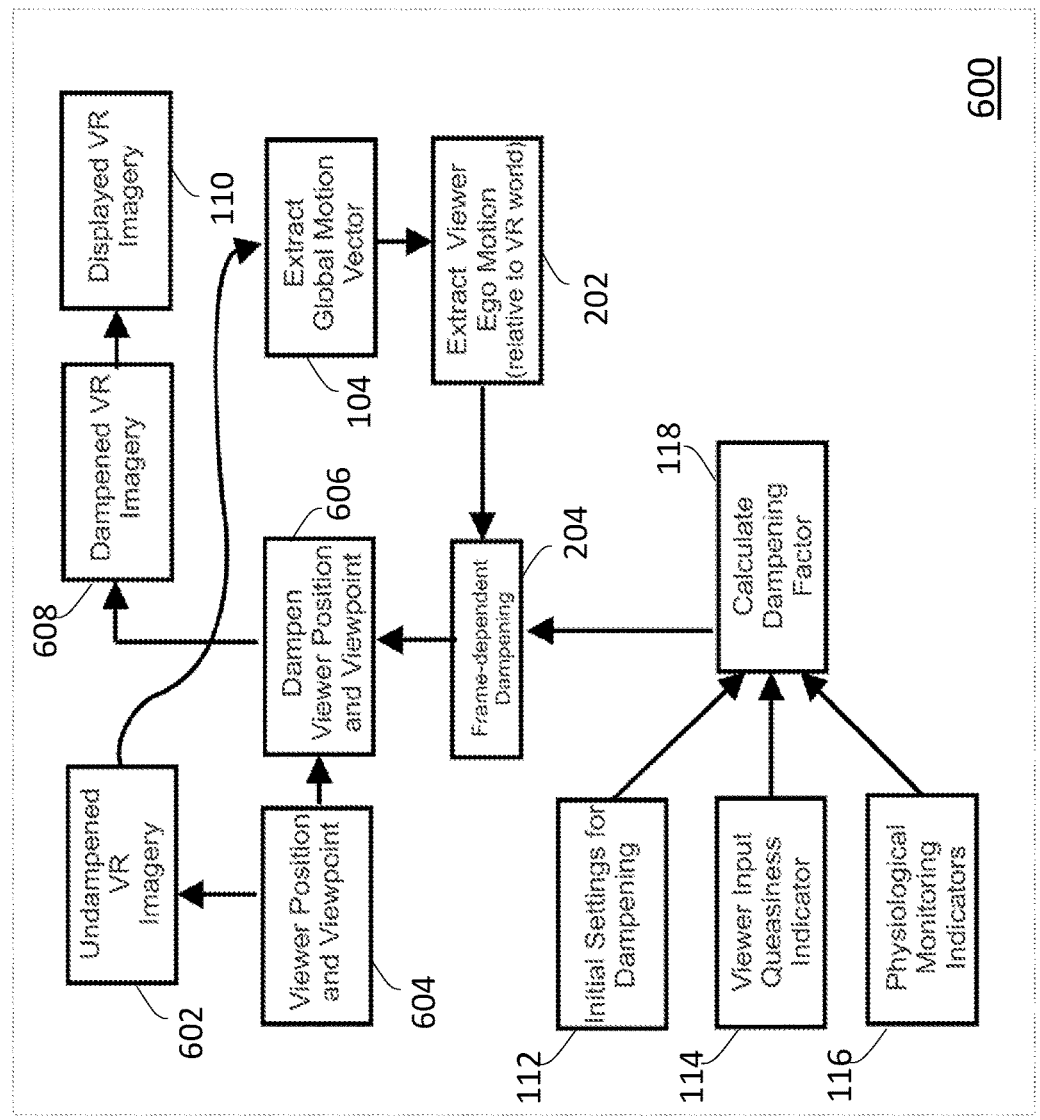

FIG. 6 illustrates an example queasiness management system 600 that can operate with a variety of VR applications including but not limited to highly interactive VR applications, etc. In some embodiments, the system (600) comprises a number of processing entities such as a dampening factor generator 118, an undampened imagery controller 604, an imagery motion extractor 104, an ego-motion extractor 202, a frame-dependent motion dampener 204, a dampened ego-motion controller 606, etc., each of which may be implemented collectively or individually with one or more computing processors. In some embodiments, the system (200) may be implemented by the system (100) of FIG. 1 or the system (200) of FIG. 2 with additional processing entities.

The systems (200 and 600) of FIG. 2 and FIG. 6 can be implemented at least in part with similar algorithm structures using similar processing entities. A difference between FIG. 2 and FIG. 6 is where dampening is applied. In contrast to what have been described in FIG. 1 and FIG. 2, dampening as performed by the system (600) is applied to a viewer's motion pathway represented in (or virtually navigating) a virtual or real world, as opposed to applying dampening to global motions extracted from input VR imagery. The viewer's motion pathway represented in the virtual or real world may comprise the viewer's position as represented in the virtual or real world, the viewer's viewpoint as represented in the virtual or real world, etc., even though the viewer may not be actually physically present in the virtual or real world (for or from which VR imagery is to be constructed or acquired).

Global motions of dampened VR imagery 608 become dampened as a result of the viewer's motion pathway being possibly dampened or changed. In an example, in a video game application that might involve flying an ornithopter, the ornithopter may not be allowed to make a sudden pitch or rapid roll, if the system (600) dynamically determines that the viewer's queasiness state would be on a state trajectory that is likely to exceed the viewer's normal range of queasiness state for the sudden pitch or the rapid roll. In another example, in a Parkour game, if the viewer/user makes a faulty move that would result in a spinning deathly fall, the rate of descent and spinning motion may be slowed to avoid onset of queasiness, if the system (600) dynamically determines that the viewer's queasiness state would be on a state trajectory that is likely to exceed the viewer's normal range of queasiness state for relatively rapid descent or relatively high spinning motion. On the other hand, if the viewer/user is a thrill seeker, the rate of descent and spinning motion may not be slowed so that the viewer/user can feel full effects of the faulty move.

In some embodiments, the undampened imagery controller (604) comprises software, hardware, a combination of software and hardware, etc., configured to determine a viewer's undampened motion pathway including the viewer's position to be represented in a virtual or real world, the viewer's viewpoint to be represented in the virtual or real world, etc. In some embodiments, the viewer's undampened motion pathway may be determined (e.g., incrementally, iteratively, etc.) based at least in part on the viewer's ego motions, which may be determined by the ego-motion extractor (202) based on the viewer's motion data collected from motion sensors, positional sensors, orientation sensors, etc. In some embodiments, the undampened imagery controller (604) controls (e.g., remote, locally, etc.) image construction or acquisition devices/processors for or in the virtual or real world to generate undampened VR imagery 602 in relation to the viewer's represented position and viewpoint on the undampened motion pathway in the virtual or real world.

In some embodiments, the imagery motion extractor (104) comprises software, hardware, a combination of software and hardware, etc., configured to receive undampened VR imagery 602 generated under the control of the undampened imagery controller (604). In some embodiments, the imagery motion extractor (104) extracts/determines global motions as represented in the undampened VR imagery (602). Additionally, optionally, or alternatively, the imagery motion extractor (104) may determine the global motions using image metadata received with the input VR imagery (102). In an example, the image metadata may specify or describe the viewer's undampened motion pathway as represented in the virtual or real world.

In some embodiments, the ego-motion extractor (202) comprises software, hardware, a combination of software and hardware, etc., configured to correlate the ego-motions with the global motions extracted from the undampened VR imagery to generate frame-dependent motions.

In some embodiments, the frame-dependent motion dampener (204) receives a dampening factor as a time sequence of dampening factor values adaptively determined by the dampening factor generator (118); applies the dampening factor to the frame-dependent motions to generate new frame-dependent motions (which may be represented by new frame-dependent motion vectors). In some cases, the (undampened) frame-dependent motions may be below a threshold (which may be specific to the viewer) and thus the global motions in the input VR imagery need not be dampened; the new frame-dependent motions may dampen, for example, the effects of the viewer's left and right head turnings on the VR imagery.

In some embodiments, the dampened ego-motion controller (606) comprises software, hardware, a combination of software and hardware, etc., configured to receive the new frame-dependent motions as determined by the frame-dependent motion dampener (204). Using the new frame-dependent motions generated with the dampening factor, the dampened ego-motion controller (606) creates or selects a specific (dampened on an as-needed basis in accordance with the dampening factor) motion pathway for the viewer including the viewer's position to be represented in a virtual or real world, the viewer's viewpoint to be represented in the virtual or real world, etc. In some embodiments, the viewer's specific motion pathway may be determined (e.g., incrementally, iteratively, etc.) based at least in part on the viewer's undampened motion pathway provided by the undampened imagery controller (604). In some embodiments, based on the viewer's specific motion pathway as dampened on the as-needed basis in accordance with the dampening factor, the dampened imagery controller (606) dampens the viewer's ego-motions that are to be represented in the virtual or real world, and controls (e.g., remote, locally, etc.) image construction or acquisition devices/processors for or in the virtual or real world to generate dampened VR imagery 608 in relation to the viewer's represented (dampened) position and viewpoint on the specific motion pathway in the virtual or real world.

In some embodiments, the system (600) receives the dampened VR imagery generated based on the viewer's specific motion pathway. In some embodiments, the dampened VR imagery may be sent to, or used by, a display (e.g., the viewer's HMD, a wearable computing device, etc.) to cause the dampened VR imagery to be rendered to the viewer, for example, as displayed VR imagery 110. The dampened VR imagery may be further mapped to the viewer's HMD (e.g., in the form of two 2D images sent to each of left and right eye views of the HMD).

7. Example Process Flows

Figure 7:
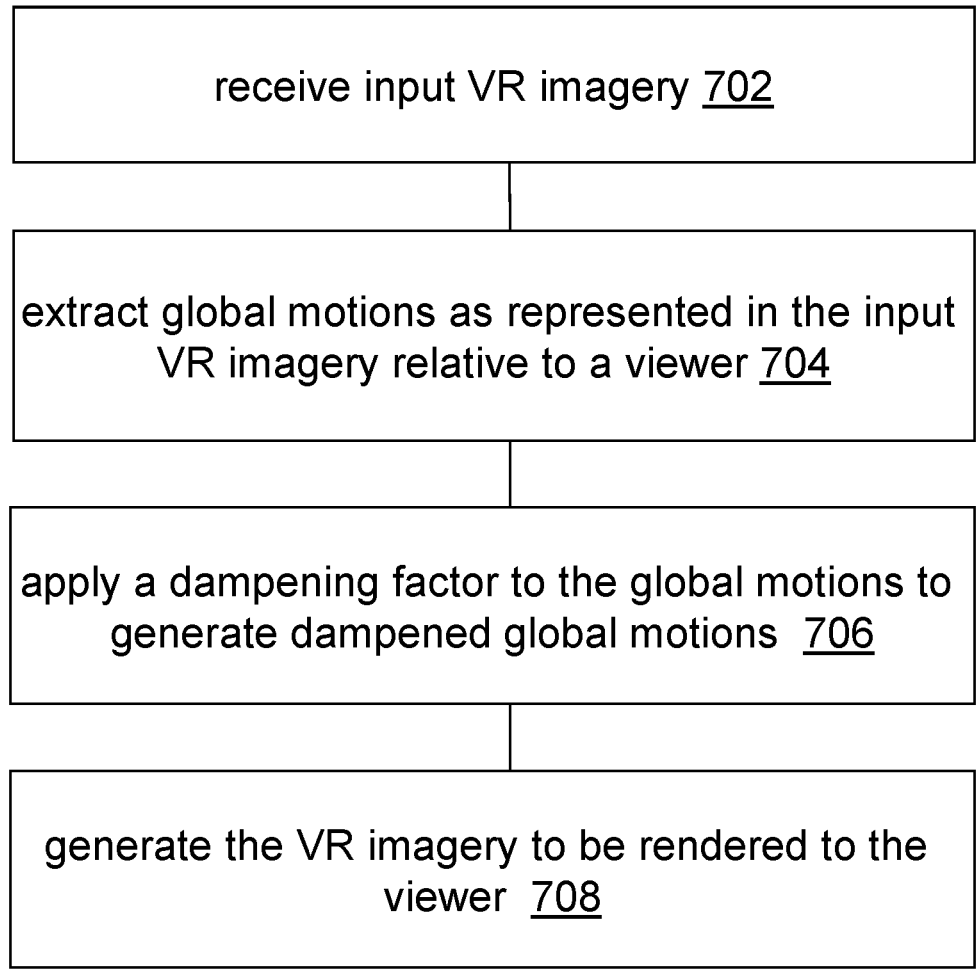
FIG. 7 illustrates an example process flows.

FIG. 7 illustrates an example process flow according to an example embodiment of the present invention. In some example embodiments, one or more computing devices or components may perform this process flow. In block 702, a queasiness management system (e.g., 100 of FIG. 1, 200 of FIG. 2, 600 of FIG. 6, etc.) receives input VR imagery.

In block 704, the queasiness management system extracts global motions as represented in the input VR imagery relative to a viewer of a virtual reality (VR) application.

In block 706, the queasiness management system applies a dampening factor to the global motions to generate dampened global motions.

In block 708, the queasiness management system generates, based on the input VR imagery and the dampened global motions, the VR imagery to be rendered to the viewer at a time point.

In an embodiment, the queasiness management system is further configured to perform: receiving input VR imagery; extracting, from the input VR imagery, global motions as represented in the input VR imagery relative to the viewer; extracting, from the viewer's motion sensor data, the viewer's ego-motions while the viewer is viewing the VR imagery; correlating the global motions extracted from the input VR imagery with the viewer's ego motions extracted from the viewer's motion sensor data to generate frame-dependent motions; applying the dampening factor to the frame-dependent motions to generate dampened frame-dependent motions.

In an embodiment, the VR imagery at the time point is generated based on the input VR imagery and the dampened frame-dependent motions.

In an embodiment, the VR imagery to be rendered at the time point is acquired or constructed based on the viewer's dampened ego-motions generated based on the dampened frame-dependent motions.

In an embodiment, the input VR imagery represents undampened VR imagery acquired with a first image acquisition device at the viewer's represented undampened location and viewpoint; the VR imagery to be rendered at the time point represents dampened VR imagery acquired with a second image acquisition device at the viewer's represented dampened location and viewpoint.

In an embodiment, the queasiness management system is further configured to perform: receiving one or more physiological monitoring indicators from the viewer up to a first time point; determining, based at least in part on the one or more physiological monitoring indicators from the viewer up to the first time point, the dampening factor to be applied to relative motions between the viewer and VR imagery to be rendered to the viewer at the time point no earlier than the first time point, the dampening factor being determined in a predictive model that comprises (1) a dynamics model that relates the viewer's previous queasiness states to the viewer's current queasiness state and (2) an observation model that relates the viewer's physiological monitoring indicators to the viewer's queasiness state; generating the VR imagery to be rendered to the viewer with the relative motions dampened in accordance with the dampening factor determined in the predictive model.

In an embodiment, the queasiness management system is further configured to perform: based at least in part on the one or more physiological monitoring indicators from a viewer up to a first time point and one or more queasiness states of the viewer up to the first time point, using the predictive model to predict the viewer's queasiness state at the time point; determining, based at least in part on the viewer's queasiness state at the time point as predicted, the dampening factor to be applied to the relative motions between the viewer and virtual reality (VR) imagery to be rendered to the viewer at the time point.

In an embodiment, the predictive model is used to further integrate view-specific initial settings and user input as entered by the viewer up to the first time point into a determination of the dampen factor to be applied to the relative motions between the viewer and virtual reality (VR) imagery to be rendered to the viewer at the time point.

In an embodiment, the one or more physiological monitoring indicators from the viewer comprise one or more of: eye tracking, pupilometry, galvanic skin response, heart rate, facial expression, thermal imaging, electroencephalogram, etc.

In an embodiment, the VR application represents one of: a VR cinema application, a VR application incorporating ego-motions, a VR application of high interactivity, a remote-presence application, a game application, an augmented reality application, etc.

In an embodiment, the VR application represents a real time application; the first time point represents a present time that most recently occurs in real time; the time point represents a future time that has not occurred in real time.

In an embodiment, the predictive model is implemented with an estimator that estimates or predicts the viewer's future queasiness state and an optimal controller that determines an optimal value for the dampening factor to control the viewer's future queasiness state below a threshold specific to the viewer.

In an embodiment, the estimator uses one of: a linear state transition function, a non-linear state transition function, etc.

In an embodiment, the observation model represents one of: a linear observation model, or a non-linear observation model.

In an embodiment, the optimal controller represents a linear quadratic Gaussian controller.

In an embodiment, the relative motions between the viewer and the VR imagery to be rendered to the viewer at the time point, as dampened by the dampening factor, represent motions at the time point in the viewer's specific motion pathway in a virtual or a represented world.

In an embodiment, the relative motions between the viewer and the VR imagery to be rendered to the viewer at the time point, as dampened by the dampening factor, comprise one or more of: linear positions, angular positions, translational velocities, rotational velocities, translational accelerations, rotational accelerations, etc.

In an embodiment, the dynamics model incorporates one or more previous values of the dampening factor as a part of inputs.

In an embodiment, the VR application represents one of: a VR cinema application, a VR application incorporating ego-motions, a VR application of high interactivity, a remote-presence application, a game application, an augmented reality application, etc.

In an embodiment, the queasiness management system is further configured to adapt the VR imagery to be rendered to the viewer at the time point to device-specific VR imagery for display to the viewer; the device-specific VR imagery is for rendering with one of: a head-mounted display, an integrated display of a computing device, a display of a wearable computing device, a mobile device, a wall display, a game display, etc.

In an embodiment, the VR imagery to be rendered to the viewer at the time point, as dampened by the dampening factor, represents one of: two-dimensional (2D) imagery, three-dimensional (3D) imagery, multi-view imagery, etc.

In various example embodiments, an apparatus, a system, an apparatus, or one or more other computing devices performs any or a part of the foregoing methods as described. In an embodiment, a non-transitory computer readable storage medium stores software instructions, which when executed by one or more processors cause performance of a method as described herein.

Note that, although separate embodiments are discussed herein, any combination of embodiments and/or partial embodiments discussed herein may be combined to form further embodiments.

8. Implementation Mechanisms—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 8:
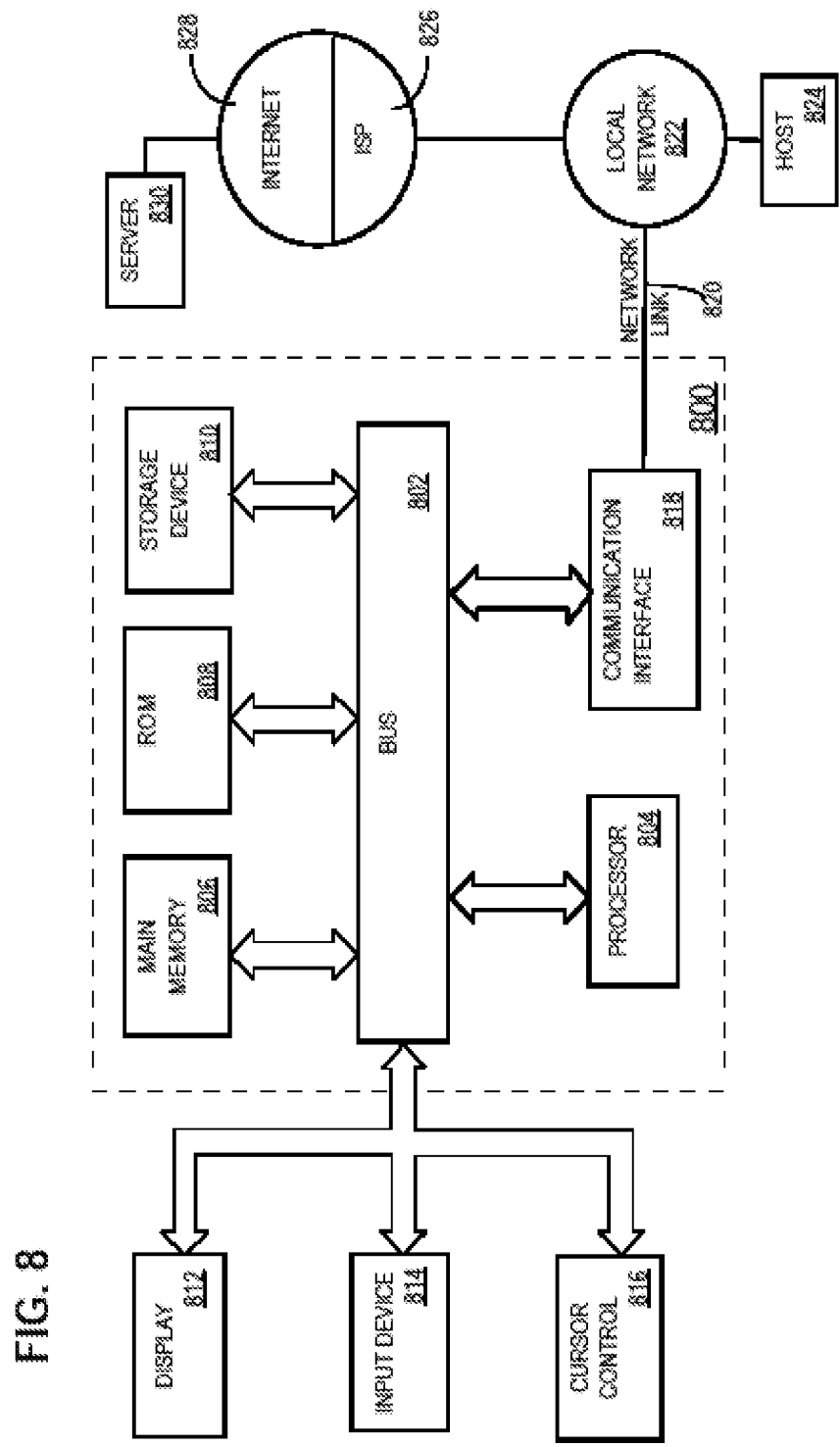
FIG. 8 illustrates an example hardware platform on which a computer or a computing device as described herein may be implemented.

For example, FIG. 8 is a block diagram that illustrates a computer system 800 upon which an example embodiment of the invention may be implemented. Computer system 800 includes a bus 802 or other communication mechanism for communicating information, and a hardware processor 804 coupled with bus 802 for processing information. Hardware processor 804 may be, for example, a general purpose microprocessor.

Computer system 800 also includes a main memory 806, such as a random access memory (RAM) or other dynamic storage device, coupled to bus 802 for storing information and instructions to be executed by processor 804. Main memory 806 also may be used for storing temporary variables or other intermediate information during execution of instructions to be executed by processor 804. Such instructions, when stored in non-transitory storage media accessible to processor 804, render computer system 800 into a special-purpose machine that is customized to perform the operations specified in the instructions.

Computer system 800 further includes a read only memory (ROM) 808 or other static storage device coupled to bus 802 for storing static information and instructions for processor 804.

A storage device 810, such as a magnetic disk or optical disk, solid state RAM, is provided and coupled to bus 802 for storing information and instructions.

Computer system 800 may be coupled via bus 802 to a display 812, such as a liquid crystal display, for displaying information to a computer user. An input device 814, including alphanumeric and other keys, is coupled to bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

Computer system 800 may implement the techniques described herein using customized hard-wired logic, one or more ASICs or FPGAs, firmware and/or program logic which in combination with the computer system causes or programs computer system 800 to be a special-purpose machine. According to one embodiment, the techniques herein are performed by computer system 800 in response to processor 804 executing one or more sequences of one or more instructions contained in main memory 806. Such instructions may be read into main memory 806 from another storage medium, such as storage device 810. Execution of the sequences of instructions contained in main memory 806 causes processor 804 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 810. Volatile media includes dynamic memory, such as main memory 806. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer can load the instructions into its dynamic memory and send the instructions over a telephone line using a modem. A modem local to computer system 800 can receive the data on the telephone line and use an infra-red transmitter to convert the data to an infra-red signal. An infra-red detector can receive the data carried in the infra-red signal and appropriate circuitry can place the data on bus 802. Bus 802 carries the data to main memory 806, from which processor 804 retrieves and executes the instructions. The instructions received by main memory 806 may optionally be stored on storage device 810 either before or after execution by processor 804.

Computer system 800 also includes a communication interface 818 coupled to bus 802. Communication interface 818 provides a two-way data communication coupling to a network link 820 that is connected to a local network 822. For example, communication interface 818 may be an integrated services digital network (ISDN) card, cable modem, satellite modem, or a modem to provide a data communication connection to a corresponding type of telephone line. As another example, communication interface 818 may be a local area network (LAN) card to provide a data communication connection to a compatible LAN. Wireless links may also be implemented. In any such implementation, communication interface 818 sends and receives electrical, electromagnetic or optical signals that carry digital data streams representing various types of information.

Network link 820 typically provides data communication through one or more networks to other data devices. For example, network link 820 may provide a connection through local network 822 to a host computer 824 or to data equipment operated by an Internet Service Provider (ISP) 826. ISP 826 in turn provides data communication services through the world wide packet data communication network now commonly referred to as the "Internet" 828. Local network 822 and Internet 828 both use electrical, electromagnetic or optical signals that carry digital data streams. The signals through the various networks and the signals on network link 820 and through communication interface 818, which carry the digital data to and from computer system 800, are example forms of transmission media.

Computer system 800 can send messages and receive data, including program code, through the network(s), network link 820 and communication interface 818. In the Internet example, a server 830 might transmit a requested code for an application program through Internet 828, ISP 826, local network 822 and communication interface 818.

The received code may be executed by processor 804 as it is received, and/or stored in storage device 810, or other non-volatile storage for later execution.

9. Equivalents, Extensions, Alternatives and Miscellaneous

In the foregoing specification, example embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A method, comprising:
   receiving input VR imagery;
   extracting global motions as represented in the input VR imagery relative to a viewer of a virtual reality (VR) application;

applying a dampening factor to the global motions to generate dampened global motions;

generating, based on the input VR imagery and the dampened global motions, VR imagery to be rendered to the viewer at a time point, wherein generating the VR imagery further comprises:

receiving one or more physiological monitoring indicators from the viewer up to a first time point;

determining, based at least in part on the one or more physiological monitoring indicators from the viewer up to the first time point, the dampening factor to be applied to relative motions between the viewer and VR imagery to be rendered to the viewer at the time point no earlier than the first time point, the dampening factor being determined in a predictive model that comprises (1) a dynamics model that relates the viewer's previous queasiness states to the viewer's current queasiness state and (2) an observation model that relates the viewer's physiological monitoring indicators to the viewer's queasiness state, wherein the predictive model is implemented with an estimator that estimates or predicts the viewer's future queasiness state and an optimal controller that determines an optimal value for the dampening factor to control the viewer's future queasiness state below a threshold specific to the viewer; and generating the VR imagery to be rendered to the viewer with the relative motions dampened in accordance with the dampening factor determined in the predictive model, wherein the method is performed by one or more computing devices.

2. The method of claim 1, further comprising:

extracting, from the viewer's motion sensor data, the viewer's ego-motions while the viewer is viewing the VR imagery;

correlating the global motions extracted from the input VR imagery with the viewer's ego motions extracted from the viewer's motion sensor data to generate frame-dependent motions;

applying the dampening factor to the frame-dependent motions to generate dampened frame-dependent motions.

3. The method of claim 2, wherein the VR imagery at the time point is generated based on the input VR imagery and the dampened frame-dependent motions.

4. The method of claim 2, wherein the VR imagery to be rendered at the time point is acquired or constructed based on the viewer's dampened ego-motions generated based on the dampened frame-dependent motions.

5. The method of claim 4, wherein the input VR imagery represents undampened VR imagery acquired with a first image acquisition device at the viewer's represented undampened location and viewpoint; and wherein the VR imagery to be rendered at the time point represents dampened VR imagery acquired with a second image acquisition device at the viewer's represented dampened location and viewpoint.

6. The method of claim 1, further comprising:

based at least in part on the one or more physiological monitoring indicators from a viewer up to a first time point and one or more queasiness states of the viewer up to the first time point, using the predictive model to predict the viewer's queasiness state at the time point;

determining, based at least in part on the viewer's queasiness state at the time point as predicted, the dampening factor to be applied to the relative motions between the viewer and virtual reality (VR) imagery to be rendered to the viewer at the time point.

7. The method of claim 1, wherein the predictive model is used to further integrate view-specific initial settings and user input as entered by the viewer up to the first time point into a determination of the dampen factor to be applied to the relative motions between the viewer and virtual reality (VR) imagery to be rendered to the viewer at the time point.

8. The method of claim 1, wherein the one or more physiological monitoring indicators from the viewer comprise one or more of: eye tracking, pupillometry, galvanic skin response, heart rate, facial expression, thermal imaging, or electroencephalogram.

9. The method of claim 1, wherein the VR application represents a real-time application; wherein the first time point represents a present time that most recently occurs in real time; and wherein the time point represents a future time that has not occurred in real time.

10. The method of claim 1, wherein the estimator uses one of: a linear state transition function, or a non-linear state transition function.

11. The method of claim 1, wherein the optimal controller represents a linear quadratic Gaussian controller.

12. The method of claim 1, wherein the relative motions between the viewer and the VR imagery to be rendered to the viewer at the time point, as dampened by the dampening factor, represent motions at the time point in the viewer's specific motion pathway in a virtual or a represented world.

13. The method of claim 1, wherein the relative motions between the viewer and the VR imagery to be rendered to the viewer at the time point, as dampened by the dampening factor, comprise one or more of: linear positions, angular positions, translational velocities, rotational velocities, translational accelerations, or rotational accelerations.

14. The method of claim 1, wherein the dynamics model incorporates one or more previous values of the dampening factor as a part of inputs.

15. The method of claim 1, wherein the observation model one of: a linear observation model, or a non-linear observation model.

16. The method of claim 1, wherein the VR application represents one of: a VR cinema application, a VR application incorporating ego-motions, a VR application of high interactivity, a remote-presence application, a game application, or an augmented reality application.

17. The method of claim 1, further comprising adapting the VR imagery to be rendered to the viewer at the time point to device-specific VR imagery for display to the viewer, wherein the device-specific VR imagery is for rendering with one of: a head-mounted display, an integrated display of a computing device, a display of a wearable computing device, a mobile device, a wall display, or a game display.

18. The method of claim 1, wherein the VR imagery to be rendered to the viewer at the time point, as dampened by the dampening factor, represents one of: two-dimensional (2D) imagery, three-dimensional (3D) imagery, or multi-view imagery.

19. An apparatus performing with one or more processors the method of claim 1.

20. A system with one or more processors performing the method of claim 1.

21. A non-transitory computer readable storage medium, storing software instructions, which when executed by one or more processors cause performance of the method recited in claim 1.

22. A computing device comprising one or more processors and one or more storage media, storing a set of instructions, which when executed by one or more processors cause performance of the method recited in claim 1.

* * * * *